US011846573B2

(12) United States Patent
Abdulla et al.

(10) Patent No.: US 11,846,573 B2
(45) Date of Patent: Dec. 19, 2023

(54) METHOD AND SYSTEM FOR HYDROCARBON SAMPLING DEVICE

(71) Applicant: SAUDI ARABIAN OIL COMPANY, Dhahran (SA)

(72) Inventors: Wasel E. Abdulla, Al Hulaylah (SA); Abdulaziz H. Aljabr, Alkhobar (SA); Eid M. Dossari, Al-Hassa (SA); Saud A. Hassan, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 28 days.

(21) Appl. No.: 17/662,954

(22) Filed: May 11, 2022

(65) Prior Publication Data

US 2023/0366788 A1    Nov. 16, 2023

(51) Int. Cl.
*G01N 1/20* (2006.01)
*G01N 33/28* (2006.01)

(52) U.S. Cl.
CPC ....... *G01N 1/2035* (2013.01); *G01N 33/2823* (2013.01); *G01N 2001/205* (2013.01)

(58) Field of Classification Search
CPC ............. G01N 1/2035; G01N 33/2823; G01N 2001/205
See application file for complete search history.

(56) References Cited

U.S. PATENT DOCUMENTS

| | | | | |
|---|---|---|---|---|
| 4,631,967 A * | 12/1986 | Welker | ................ | G01L 19/0007 73/866.5 |
| 5,134,879 A * | 8/1992 | Wong | ................. | G01N 15/0618 73/863.85 |
| 5,138,755 A * | 8/1992 | Evans | ................. | B25B 27/0028 29/256 |
| 5,161,417 A * | 11/1992 | Strong | ................. | G01N 1/2035 73/863.31 |
| 6,357,470 B1 * | 3/2002 | Evans | ................. | G01N 17/046 422/53 |
| 7,617,745 B1 * | 11/2009 | Mayeaux | ............. | G01N 1/2035 73/866.5 |
| 2004/0099143 A1 * | 5/2004 | Welker | ............... | G01N 33/0014 96/413 |
| 2015/0204762 A1 * | 7/2015 | Al Najrani | ............... | G01N 7/00 73/863.86 |
| 2020/0232887 A1 * | 7/2020 | Atchison | .............. | G01N 1/2035 |

* cited by examiner

*Primary Examiner* — Kristina M Deherrera
*Assistant Examiner* — Jean F Morello
(74) *Attorney, Agent, or Firm* — Osha Bergman Watanabe & Burton LLP

(57) ABSTRACT

A portable hydrocarbon sampling device may include a first housing with a first bore, a valve housing with a second bore coupled to the first housing, and a cross-flow housing with a third bore coupled to the valve housing to form a continuous flow path. The valve housing includes a valve to open and close the second bore. A cross bore may be coupled to the cross-flow housing, and is perpendicular to the third bore. A probe may be disposed within the continuous flow path and in fluid communication with the cross bore. An actuator housing may be coupled to the cross-flow housing. The actuator housing may include an actuator to extend into the probe. A sampling container fluidly may be coupled to the cross bore at end distal to the cross-flow housing. The sampling container may be configured to collect the fluids from the probe.

20 Claims, 8 Drawing Sheets

METHOD AND SYSTEM FOR HYDROCARBON SAMPLING DEVICE

BACKGROUND

In the oil and gas industry, hydrocarbon sampling may refer to taking samples of hydrocarbons in the field for analysis to determine various fluid properties. Accurately sampling hydrocarbons, such as, crude oil and natural gas, in the field for laboratory analysis is critical to ensuring product quality and regulations are being meet and maintained.

Typically, samples of the hydrocarbons are taken while the hydrocarbons are flowing, such as when the hydrocarbons are being transported through a pipeline. Conventional hydrocarbon sampling devices may require cumbersome installation with a major expense for long term use. Thus, not all pipelines cannot accommodate conventional hydrocarbon sampling devices installation because of congested area, inadequate pipe straight length, cost, and other factors. Additionally, the conventional hydrocarbon sampling devices may have to be routinely maintained such as preventive maintenance, obsolescence replacement program, inspections, and other non-productive time (NPT) operations. Therefore, conventional methods make it impractical to provide conventional hydrocarbon sampling devices in certain pipelines as long-term expenses may be greatly increased as well as increase the day-to-day operating expenses.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, the embodiments herein relate to a method for conducting a hydrocarbon sampling operation on a pipeline. The Method may include removably coupling a portable hydrocarbon sampling device to the pipeline to access a vent of the pipeline; actuating an actuator of the portable hydrocarbon sampling device in a first direction to extend a probe of the portable hydrocarbon sampling device into a bore of the pipeline through the vent; drawing hydrocarbons flowing in the bore into the probe and pushing the hydrocarbons up the probe and into a cross bore with a differential pressure between the bore and a sampling container fluidly coupled to the cross bore; and obtaining a hydrocarbon sample by collecting the hydrocarbons in the sampling container.

In another aspect, the embodiments herein relate to a portable hydrocarbon sampling device. The portable hydrocarbon sampling device may include a first housing with a first bore; a valve housing with a second bore coupled to the first housing, the valve housing comprises a valve to open and close the second bore; a cross-flow housing with a third bore coupled to the valve housing, wherein the first bore, the second bore, and the third bore form a continuous flow path; a cross bore coupled to the cross-flow housing, wherein the cross bore is perpendicular to the third bore; a probe disposed within the continuous flow path and in fluid communication with the cross bore; an actuator housing coupled to the cross-flow housing, the actuator housing comprises an actuator to extend into the probe; and a sampling container fluidly coupled to the cross bore at end distal to the cross-flow housing, the sampling container is configured to collect the fluids from the probe.

In yet another aspect, the embodiments herein relate to a system that may include a pipeline defining a bore with hydrocarbons flowing therein, the pipeline includes a plurality of vents; and a portable hydrocarbon sampling device removably coupled to the pipeline at a location of a vent of the plurality of vents. The portable hydrocarbon sampling device may include a first housing with a first bore and an opening coaxial with the vent; a valve housing with a second bore coupled on top of the first housing, the valve housing comprises a valve to open and close the second bore; a cross-flow housing with a third bore coupled on top of the valve housing, the first bore, the second bore, and the third bore form a continuous flow path in fluid communication with the bore; a cross bore coupled to the cross-flow housing, the cross bore is perpendicular to the third bore; a probe disposed within the continuous flow path and in fluid communication with the cross bore and bore; an actuator housing coupled on top of the cross-flow housing, the actuator housing includes an actuator configured to extend the probe into the bore; and a sampling container fluidly coupled to the cross bore at end distal to the cross-flow housing, the sampling container is configured to collect the hydrocarbons from the probe.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
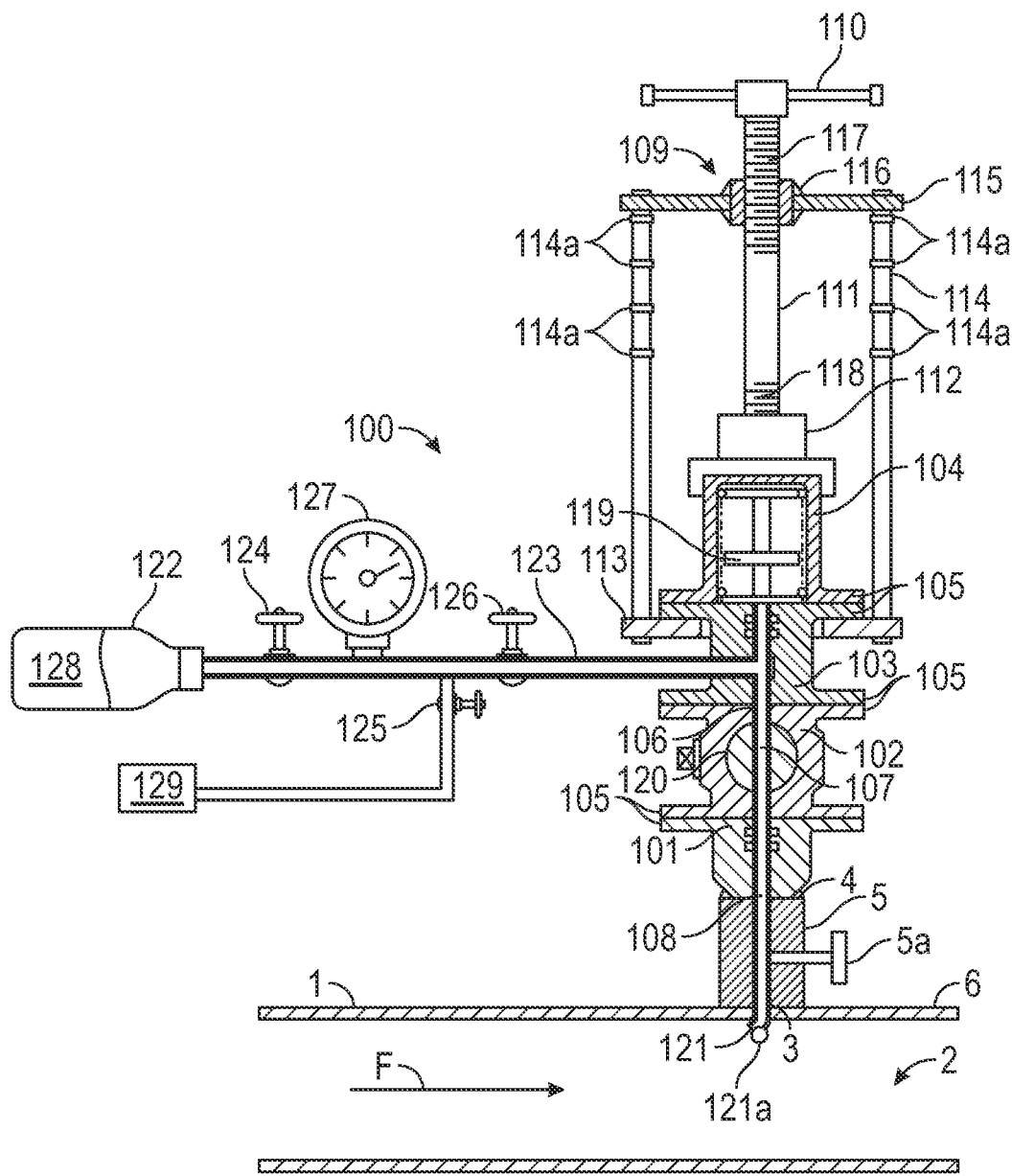
FIG. 1 illustrates a schematic cross-sectional diagram of a portable hydrocarbon sampling device in accordance with one or more embodiments of the present disclosure.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include systems and methods for retrieving hydrocarbon samples with a portable hydrocarbon sampling device. In some embodiments, the portable hydrocarbon sampling device may be installed along a pipeline to retrieve samples of hydrocarbons flowing through the pipeline. For example, a housing of the portable hydrocarbon sampling device may be installed over a vent of the pipeline to fluidly couple a sampling container of the portable hydrocarbon sampling device to a bore of the pipeline. Additionally, a probe of the portable hydrocarbon sampling device extends into the bore to retrieve the hydrocarbon samples. Additionally, a valve of the portable hydrocarbon sampling device may direct fluid flow within the portable hydrocarbon sampling device to the collect the hydrocarbon samples in the sampling container. Further, the portable hydrocarbon sampling device may include a double block and bleed along with pressure monitoring to increase safety measures within the portable hydrocarbon sampling device.

In one or more embodiments, the portable hydrocarbon sampling device according to embodiments herein may include two or more housings. The two or more housings may include, for example, a first housings having a flow bore or passage therethrough, including an inlet and an outlet end, as well as a second housings having a flow bore or passage therethrough, including an inlet and an outlet end. The two or more housings may also include cross-bores, such as for insertion of valve elements or to connect to additional flow components.

Conventional methods are limited by pre-installed sampling points at fixed points on the pipeline. However, conventional methods are inaccurate at lowest points of the pipeline as well as only being able to acquire samples with conventional hydrocarbon sampling devices at a 3 or 6 o-clock position on the pipeline. However, by using the portable hydrocarbon sampling device disclosed herein, some embodiments may use any vent on a pipeline to access the bore to retrieve hydrocarbon samples. Additionally, the portable hydrocarbon sampling device may advantageously retrieve hydrocarbon samples at any position on the pipeline ranging from a bottom of the pipeline to a top of the pipeline. Thus, the portable hydrocarbon sampling device provides a flexible, safe, reliable and portable sampling method.

Turning to FIG. 1, FIG. 1 shows a schematic cross-sectional diagram in accordance with one or more embodiments. As shown in FIG. 1, a bore 2 defined by a pipeline 1 may have fluids flowing therein. For example, hydrocarbons, such as crude oil and natural gas, may flow (see arrow F) through the bore 2. Additionally, the pipeline 1 may include a plurality of vents (3) along the length of the pipeline 1. For example purposes, only one vent 3 is shown in FIG. 1. The vent 3 may be used as an access point for a vent valve 5 to be installed on the pipeline 1. The vent valve 5 may be removably coupled to an outer surface 6 of the pipeline 1 to cover and prevent debris from entering the pipeline 1 at the vent 3. With the vent valve 5, the vent 3 may allow for air trapped in the pipeline 1 to be released. For example, an actuation device 5a, such as a hand wheel, of the vent valve 5 is actuated to release air out of the pipeline 1 through the vent valve 5.

Retrieving a sample of the hydrocarbons plays an important role to determine if the quality of the hydrocarbons is meeting governmental and product requirements. The hydrocarbon sample represents a portion of the product to test for the water, oil, contaminants, and other fluid proprieties. The hydrocarbon sample plays a pivotal role in hydrocarbon sales as a small error may result in the loss of the product. Thus, to correctly represent the product of the hydrocarbons, samples should be taken from the pipeline 1 in flowing conditions.

To retrieve hydrocarbon samples, a portable hydrocarbon sampling device 100 may be removably fixed to the pipeline 1. The pipeline 1 (or a section of the pipeline with the vent 3) is above ground, thereby having the pipeline exposed so that the portable hydrocarbon sampling device 100 may be coupled to the pipeline 1 to cover the vent 3. In one or more embodiments, when the pipeline 1 is underground (i.e., a buried pipeline), an excavation operation may be conducted to expose the pipeline 1 so that the portable hydrocarbon sampling device 100 may be coupled to the pipeline 1. In some embodiments, the buried pipeline may be designed to have portions of the pipeline 1 above ground to expose the vent 3 of the pipeline 1 to an atmosphere to allow the portable hydrocarbon sampling device 100 cover the vent 3.

In one or more embodiments, the portable hydrocarbon sampling device 100 may be removably coupled to the pipeline 1. For example, a first housing 101 of the portable hydrocarbon sampling device 100 is disposed on top of the vent valve 5. A bottom end of the first housing 101 may be removably coupled a top end of the vent valve 5 via mechanical fasteners 4, such as threaded connections, bolts, nuts, screws, studs, magnets, adhesives, and other type of non-permanent fasteners. The vent valve 5 may be in a closed position when the first housing 101 is installed to provide a safety measure and not expose the fluids within the pipeline 1. Alternatively, if there is no vent valve 5, the first housing 101 is directly coupled to the outer surface 6 over the vent 3. One skilled in the art will appreciate how the portable hydrocarbon sampling device 100 may be installed on any vent 3 along the pipeline 1.

As illustrated in FIG. 1, the portable hydrocarbon sampling device 100 may include multiple housings, including a first housing 101, a valve housing 102, a cross-flow housing 103, and an actuator housing 104. The first housing 101 may be coupled to the pipeline 1, the valve housing 102 may be coupled on top of the first housing 101, the cross-flow housing 103 may be coupled on top of the valve housing 102, and the actuator housing 104 may be coupled on top of the cross-flow housing 103. Each of the housings (101-104) may have flanges 105 such that adjacent housings may be connected the corresponding housing with the flanges 105. The flanges 105 may be coupled together via mechanical fasteners, such as threaded connections, bolts, nuts, screws, studs, magnets, adhesives, and other type of non-permanent fasteners. Additionally, a continuous flow path 106 (internal) from the first housing 101 to the cross-flow housing 103 may be provided. Additionally, the continuous flow path 106 also includes the bore of the vent valve 5. The continuous flow path 106 may be coaxial with the vent 3.

In some embodiments, the first housing 101 may have an opening 108 to seal around the vent valve 5. The opening 108 may be centered about the vent valve 5. The valve housing 102 includes a valve 120 in fluid communication with the continuous flow path 106. The valve 120 may be an isolation valve, such as a gate, globe, ball, or butterfly valve, to stop or start a flow within the portable hydrocarbon sampling device 100. The valve 120 is shown in an open position in FIG. 1 to allow flow.

The cross-flow housing 103 may include a cross bore 123 intersecting with the continuous flow path 106. Valve elements 124, 125, 126 may be disposed within the cross bore 123 to form a double block and bleed valve configuration. The valve elements 124 and 126 may be block valves and the valve element 125 may be a bleed valve. The double block and bleed valve configuration may be used to ensure that there is zero pressure when a sampling container 122 containing a fluid sample 128 is removed. By having the pressure at zero within the sampling container 122, the sampling container 122 may be safely removed without the risk of a pressure blowout. The sampling container 122 may be coupled to an end of the cross bore 123 distal to the cross-flow housing 103. The sampling container 122 may be any type of storage device to hold fluids, such as a tank or bottle. It is further envisioned that the sampling container 122 includes a check valve to ensure the fluid sample 128 does not flow back into the cross bore 123. Further, the sampling container 122 may include a seal to hermetically seal the sampling container 122 from a surrounding environment to avoid contaminating the fluid sample 128. The valve elements 124 and 126 may be used to block both an upstream and downstream in the cross bore 123, and then the valve element 125 may be used bleed any pressure that remains in the cross bore 123.

In some embodiments, a pressure gauge or sensor 127 may be attached to the cross bore 123 to continuously monitor the pressure within the cross-flow housing 103. The pressure sensor 127 may be used to determine when the sampling container 122 is full. For example, once the pressure sensor 127 reads a pressure equivalent to a pressure within the pipeline 1, the sampling container 122 is then full and a user can determine that the fluid sample 128 is collected. With the fluid sample 128 collected, the valve elements 124 and 126 may be used to block both an upstream and downstream in the cross bore 123, and then the valve element 125 may be used bleed any pressure that remains in the cross bore 123 to ensure that there is zero pressure. After confirming there is zero pressure in the cross bore 123 via the pressure sensor 127, the user may remove the sampling container 122 and send the collected fluid sample to a laboratory for analysis.

In one or more embodiments, an actuator 109 of the actuator housing 104 may include a torque connection 110 (e.g., a hand wheel or a portable pneumatic/electric actuator=) and a rod 111 attached to the actuator housing 104 via a cap 112. Additionally, a bottom plate 113 of the actuator 109 may be attached to the flange 105 of the cross-flow housing 103. Guide rods 114 may extend upward from the bottom plate 113 to a top plate 115. Additionally, the guide rods 114 may include various locking devices 114a such a notch or ledge to lock the top plate 115 at a certain height thereby limiting a distance the rod 111 may axially travel upward or downward. The top plate 115 may be locked at height on the guide rods 114 based on a size of the pipeline 1 (i.e., the inner diameter of the pipeline 1). Top threads 117 of the rod 111 may be threadedly coupled to a center block 116 of the top plate 115. Bottom threads 118 of the rod 111 may be threadedly coupled to the cap 112.

Still referring to FIG. 1, a probe 107 extends downward from the actuator housing 104 through the continuous flow path 106 and the opening 108 in the first housing 101 to enter the pipeline 1 via the vent 3. The probe 107 may be coupled to an actuation plate 119 within the actuator housing 104. The probe 107 extends downward from the actuation plate 119 into the continuous flow path 106. The probe 107 includes an inlet nozzle 121 to receive fluids from the pipeline 1. The inlet nozzle 121 may be angled from the opening 108 to face the fluid flow within the pipeline 1. The inlet nozzle 121 may extent to reach any depth/level inside the pipeline 1. It is further envisioned that the inlet nozzle 121 may include a position sensor 121a, such as a depth encoder, to determine when the inlet nozzle 121 reaches a required depth within the pipeline 1. The required depth may be based on a composition of the fluids within the pipeline 1 to avoid less water entering the fluid sample 128. For example, the torque connection 110 is torqued to axially move the rod 111 downward or upward causing the actuation plate 119 to move thereby moving the probe 107 to position the inlet nozzle 121 at the required depth. The torque connection 110 may be manually or automatically torqued.

In one or more embodiments, as the rod 111 axially moves downward, the actuation plate 119 axially moves downward to extend the probe 107 into the pipeline 1 until the inlet nozzle 121 reaches the required depth. The position sensor 121a may send an alert when the required depth is reached or missed. The rod 111 may be axially moved upward or further downward to adjust the depth of the inlet nozzle 121 until the position sensor 121a sends the alert that the required depth is reached. With the inlet nozzle 121 at the required depth in the pipeline 1, fluids may flow from the pipeline 1 and into the probe 107 based on a differential pressure between the pipeline 1 and the sampling container 122. Based on the differential pressure the fluids travel up the probe 107 and into the cross bore 123 to enter the sampling container 122 as the fluid sample 128. Once the sampling container 122 is filled with the fluid sample 128 and the pressure sensor 127 reads a pressure equivalent to the pressure within the pipeline 1, the valve elements 124 and 126 may be actuated to stop flow within the cross bore 123. With the flow stopped, the sampling container 122 may be detached from the cross bore 123, sealed, and transported to a laboratory for analysis. In some embodiments, if there is no pressure in the pipeline 1, a suction device 129 may be attached to the valve element 125 to allow samples to be taken from the pipeline 1 at zero pressure. For example, the suction device 129 may be a vacuum tanker to drawn fluids from the pipeline 1 into the sampling container 122.

Figure 2:
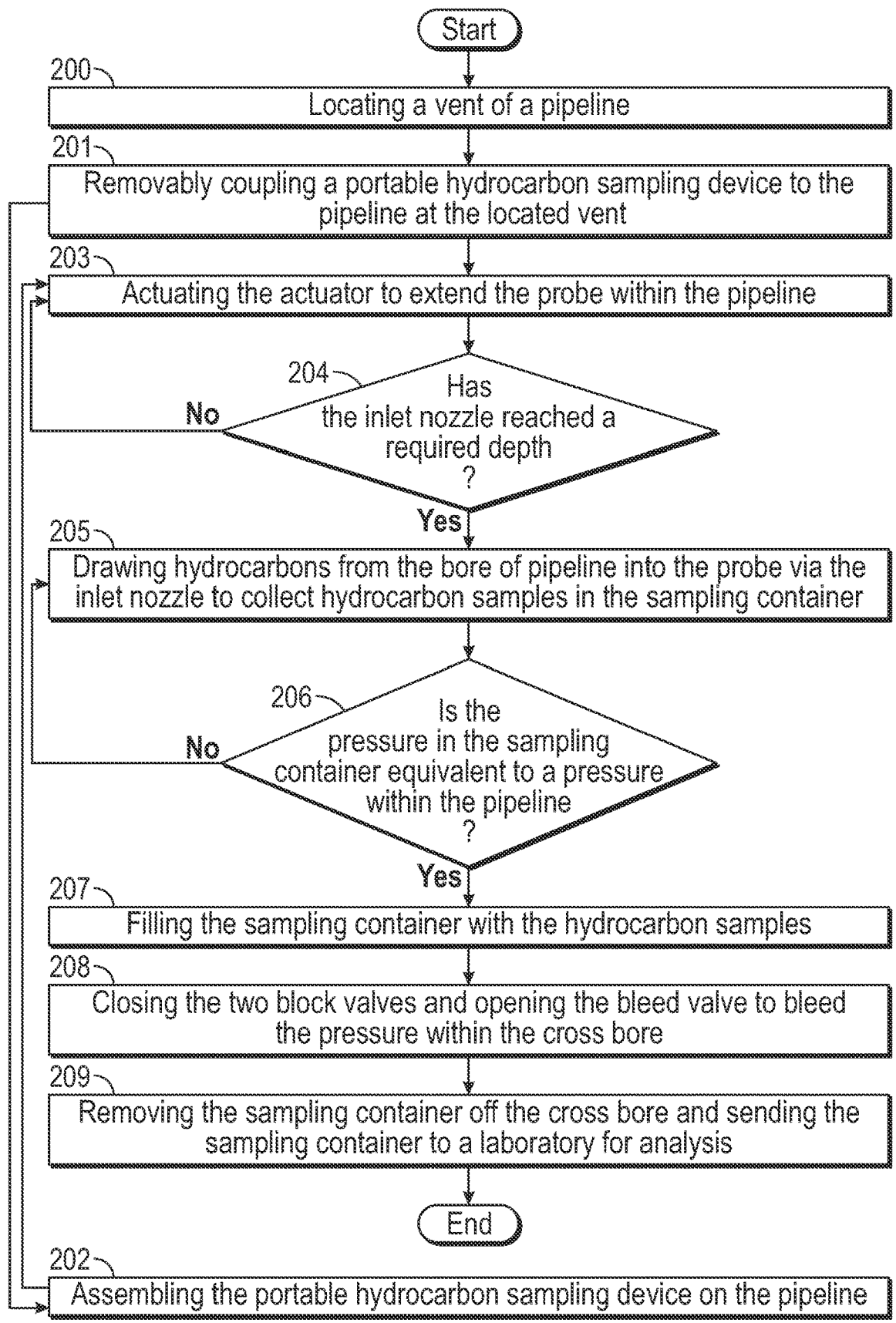
FIG. 2 illustrates a flowchart in accordance with one or more embodiments of the present disclosure.

Referring to FIG. 2, is a flowchart showing a method of using the portable hydrocarbon sampling device (100) of FIG. 1 to conduct a hydrocarbon sampling operation. One or more blocks in FIG. 2 may be performed a work at the site of pipeline (1) or by one or more components (e.g., a computing system coupled to a controller in communication with the portable hydrocarbon sampling device 100). For example, a non-transitory computer readable medium may store instructions on a memory coupled to a processor such that the instructions include functionality for conducting the hydrocarbon sampling operation. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 200, a vent of a pipeline is located based on when a hydrocarbon sample is needed. For example, if the hydrocarbon sample is need after a certain amount distance or time the hydrocarbon is flowing in the pipeline, the vent nearest to the position of the pipeline corresponding to the distance or time at which the hydrocarbon sample is need is located. The hydrocarbon sample may be taken at a vent of the pipeline approximate a transfer point where the hydrocarbon exiting the pipeline and being transfer to another location (e.g., work facilities, power plants, storage tanks, another pipeline, and other locations needing hydrocarbons). In some embodiments, if the pipeline is buried, an excavation operation may be conducted to remove portions of land above the pipeline to expose the pipeline.

In Block 201, a portable hydrocarbon sampling device is removably coupled to the pipeline at the located vent. For example, the portable hydrocarbon sampling device may be removably coupled to a vent valve on an outer surface of the pipeline. The vent valve covers the vent and allows air trapped in the pipeline to escape. The vent valve provides a conduit to place the portable hydrocarbon sampling device in fluid communication with the pipeline. The portable hydrocarbon sampling device may be transported to the location of the vent fully assembled.

As shown in Block 202, in some embodiments, each component of the portable hydrocarbon sampling device may be assembled on site at the location of the vent. For example, a first housing of the portable hydrocarbon sampling device is coupled to the vent valve via mechanical fasteners, such as threaded connections, bolts, nuts, screws, studs, magnets, adhesives, and other type of non-permanent fasteners. An opening of the first housing may be centered on the vent valve which is coaxial with the vent. Additionally, a bore of the first housing is fluidly coupled to a bore of the vent valve.

Next, a valve housing may be coupled on top of the first housing. For example, lower flanges of the valve housing mate on top of the flanges of the first housing and a mechanical fastener, such as threaded connections, bolts, nuts, screws, studs, magnets, adhesives, and other type of non-permanent fasteners, may be used to couple the flanges together. Additionally, the valve housing may be coaxially with the first housing. Further, the valve housing may be installed with the valve in the closed position. With the valve housing installed on the first housing, a cross-flow housing may be coupled on top of the valve housing. For example, bottom flanges of the cross-flow housing mate on top of upper flanges of the valve housing and a mechanical fastener, such as threaded connections, bolts, nuts, screws, studs, magnets, adhesives, and other type of non-permanent fasteners, may be used to couple the flanges together. Additionally, the cross-flow housing may be coaxially with the valve housing.

With the first housing, the valve housing, and the cross-flow housing being coaxially, a continuous flow path is formed to fluidly communicate with a bore of the pipeline via the vent valve and the vent. Additionally, a cross bore is coupled to the cross-flow housing to be perpendicular to and in fluid communication with the continuous flow path. Further, the cross bore may have a double block and bleed valve configuration. A pressure sensor may be attached to the cross bore to monitor pressure in the cross bore. At an end of the cross bore distal to the cross-flow housing, a sampling container is provided to collect hydrocarbon samples.

Next, the valve of the valve housing is moved to the open position so that an actuator housing may be coupled on top of the cross-flow housing and a probe extending from the actuator housing is inserted into the continuous flow path. For example, bottom flanges of the actuator housing mate on top of upper flanges of the cross-flow housing and a mechanical fastener, such as threaded connections, bolts, nuts, screws, studs, magnets, adhesives, and other type of non-permanent fasteners, may be used to couple the flanges together. Additionally, the probe may be coupled to an actuation plate of the actuator housing. Further, an inlet nozzle of the probe extends into the pipeline to provide fluid conduit from the bore of the pipeline to the sampling container. Additionally, an actuator may be coupled the actuator housing. For example, a bottom plate of the actuator may be coupled to the upper flanges of the cross-flow housing. Guide rods extend upward from the bottom plate to a top plate where the top plate guides a torque connection (e.g., a hand wheel) and a rod to the actuator housing via a cap. Additionally, the top plate may be locked at height on the guide rods based on a size (i.e., the inner diameter) of the pipeline. For example, the top plate may be locked on various locking devices, such a notch or ledge, of the guide rods at a certain height thereby limiting a distance the rod may axially travel upward or downward.

In Block 203, with the portable hydrocarbon sampling device removably coupled to the pipeline, the actuator is actuated to extend the probe. For example, the torque connection is torqued in a first direction to move the rod axially downward which is turn moves the actuation plate within the actuator housing axially downward. The actuation plate moves the probe downward to position an inlet nozzle of the probe within the bore of the pipeline.

In Block 204, the position of the inlet nozzle is checked to ensure that a required depth is reached via a position sensor coupled to the inlet nozzle. The required depth may be based on a composition of the fluids within the pipeline to avoid less water being collected. If the inlet nozzle has not reached the position, the position sensor will send an alert to a user to repeat Block 203 to adjust the position of the inlet nozzle. For example, the torque connection is torqued in the first direction or a second direction to move the rod axially downward or upward to move the actuation plate thereby moving the probe in the corresponding direction. Once the position of the inlet nozzle reached the required depth, the position sensor will send an alert to procced to Block 205.

In Block 205, with the inlet nozzle at the required depth, hydrocarbons from the bore of pipeline are drawn into the probe via a differential pressure between the bore and the sampling container. The inlet nozzle may be angled to face against a direction of flow within the bore to receive the hydrocarbons. With hydrocarbons entering the probe via the inlet nozzle, the hydrocarbons travel up the probe, into the cross bore, and collected into the sampling container. In some embodiments, if the pressure in the pipeline is zero, a suction device, such as a vacuum tanker, may be attached to the bleed valve to allow samples to be taken from the pipeline at zero pressure. For example, the suction device may be operated to drawn fluids from the pipeline into the sampling container via a suction force.

In Block 206, as the hydrocarbons are being collected in the sampling container, a pressure in the sampling container is measured, with a pressure sensor attached to the cross bore, to determine if the pressure equivalent to a pressure within the pipeline. If the measured pressure is not equivalent, the method may repeat Block 205. Once the measure pressure does become equivalent, the sampling container is now full with the collected hydrocarbon samples, as shown in Block 207.

In Block 208, with the hydrocarbon samples collected within the sampling container, the two block valves may be moved to a closed position to stop flow both upstream and downstream in the cross bore, and then the bleed valve between the two block valves is opened to bleed the pressure within the cross bore to reach zero pressure. Additionally, before closing the two block valves, the vent valve is closed to prevent an more fluids from the pipeline entering the portable hydrocarbon sampling device. The pressure sensor is further used to determine if the pressure has reached zero. If the pressure has not reached zero, the bleed valve continues to bleed the pressure.

In Block 209, once the pressure has reached and if confirmed by the pressure sensor, the sampling container is removed off the cross bore and sent to a laboratory for analysis. For example, the two block valves may be closed so that the sampling container may be decoupled off the cross bore. In some embodiments, a second sampling container may be coupled to the distal end of the cross bore to repeat Blocks 203-209 if more hydrocarbon samples are required. However, if no more hydrocarbon samples are required, the portable hydrocarbon sampling device may be disassembled to be stored or sent to another location to take further hydrocarbon samples at different vent of the pipeline.

Figure 3:
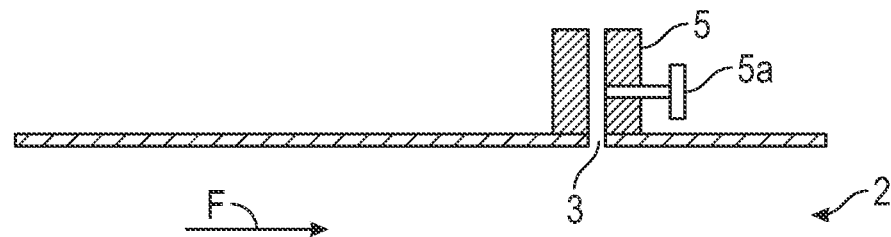
FIGS. 3-10 illustrate a hydrocarbon sampling operation using the portable hydrocarbon sampling device of FIG. 1 in accordance with one or more embodiments of the present disclosure.

Now referring FIGS. 3-10, in one or more embodiments, FIGS. 3-10 illustrate a system of implementing the method described in the flowchart of FIG. 2 using the portable hydrocarbon sampling device (100) of FIG. 1. As shown in FIG. 3, in an initial step, the vent 3 of pipeline 1 is located to determine where the portable hydrocarbon sampling device is to be installed. In some embodiments, the vent valve 5 may be installed on the vent 3.

Figure 4:
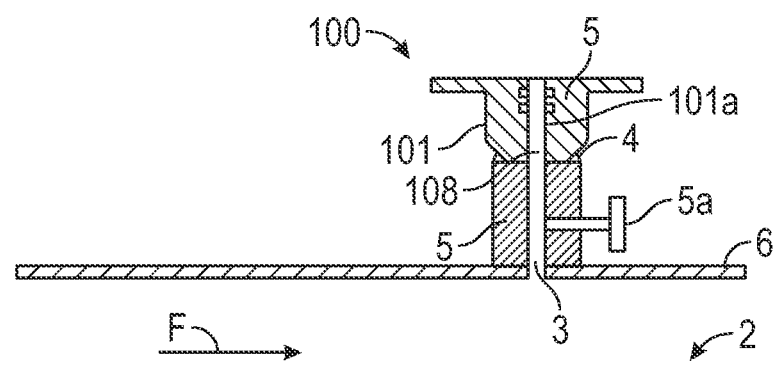

Now turning to FIG. 4, with the vent 3 located, the first housing 101 of the portable hydrocarbon sampling device (100) is removably coupled to the vent valve 5 on an outer surface 6 of the pipeline 1. The mechanical fasteners 4, such as threaded connections, bolts, nuts, screws, studs, magnets, adhesives, and other types of non-permanent fasteners, may be used to removably couple a bottom end of the first housing 101 to a top end of the vent valve 5. Additionally, the opening 108 of the first housing 101 may be centered on the vent valve 5 to have a bore 101a of the first housing 101 coaxial with the vent 3.

Figure 5:
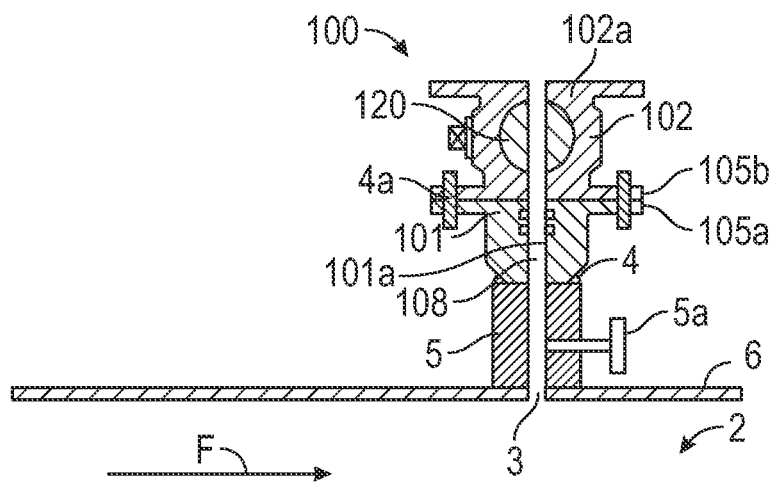

As shown in FIG. 5, the valve housing 102 may be coupled on top of the first housing 101. The lower flanges 105b of the valve housing 102 mate on top of the upper flanges 150a of the first housing 101 and a mechanical fastener 4a, such as threaded connections, bolts, nuts, screws, studs, magnets, adhesives, and other type of non-permanent fasteners, may be used to couple the flanges (105a-b) together. Additionally, a bore 102a of the valve housing 102 is aligned to be coaxially with the bore 101a of the first housing 101. Further, the valve 120 of the valve housing 102 may be in a closed position to ensure no fluids exit the portable hydrocarbon sampling device (100) during assembly.

Figure 6:
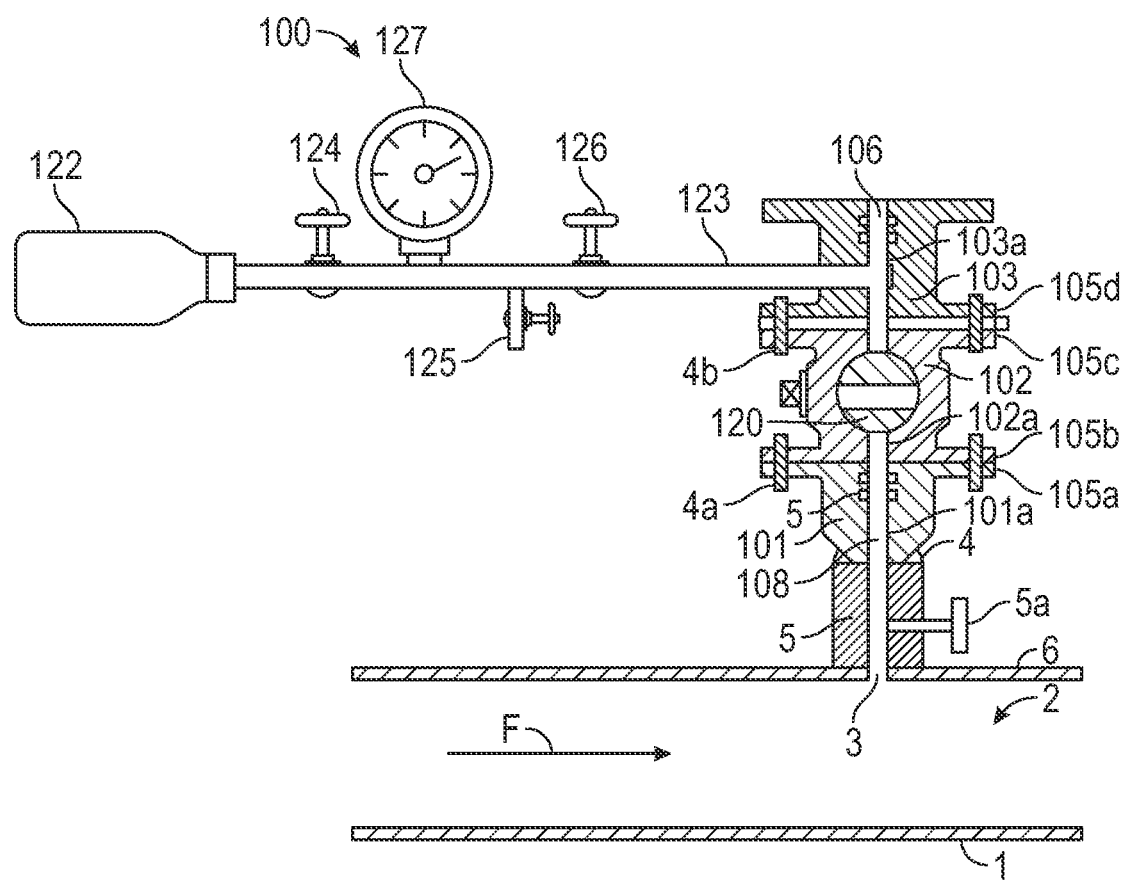

Referring to FIG. 6, with the valve housing 102 installed on the first housing 101, the cross-flow housing 103 may be coupled on top of the valve housing 102. The bottom flanges 105d of the cross-flow housing 103 mate on top of the upper flanges 105c of the valve housing 102. The mechanical fastener 4b may be used to couple the flanges (105c-d) together. Additionally, a bore 103a of the cross-flow housing 103 is aligned to be coaxial with the bore 102a of the valve housing 102. With the first housing 101, the valve housing 102, and the cross-flow housing 130 being coaxially aligned, the corresponding bores (101a, 102a, 103a) of each housing (101, 102, 103) form the continuous flow path 106 in fluid communication with the bore 2 of the pipeline 1 via the vent 3.

Still referring to FIG. 6, the cross bore 123 is coupled to the cross-flow housing 103 to be perpendicular to the bore 103a and in fluid communication with the continuous flow path 106. The cross bore 123 may include the valve elements 124, 125, 126 to form a double block and bleed valve configuration. For example, valve elements 124 and 126 may be block valves while valve element 125 may be a bleed valve. The valve elements 124 and 126 may be used to block both an upstream and downstream in the cross bore 123, and then the valve element 125 may be used bleed any pressure that remains in the cross bore 123. Additionally, the sampling container 122 may be coupled to an end of the cross bore 123 distal to the cross-flow housing 103. For example, an end of the sampling container 122 may include threads to be threaded onto corresponding threads of the end of the cross bore 123. Further, the pressure sensor 127 may be attached to the cross bore 123, between valve elements 124 and 126, to continuously monitor the pressure within the cross-flow housing 103 to ensure required pressures are maintained.

Figure 7:
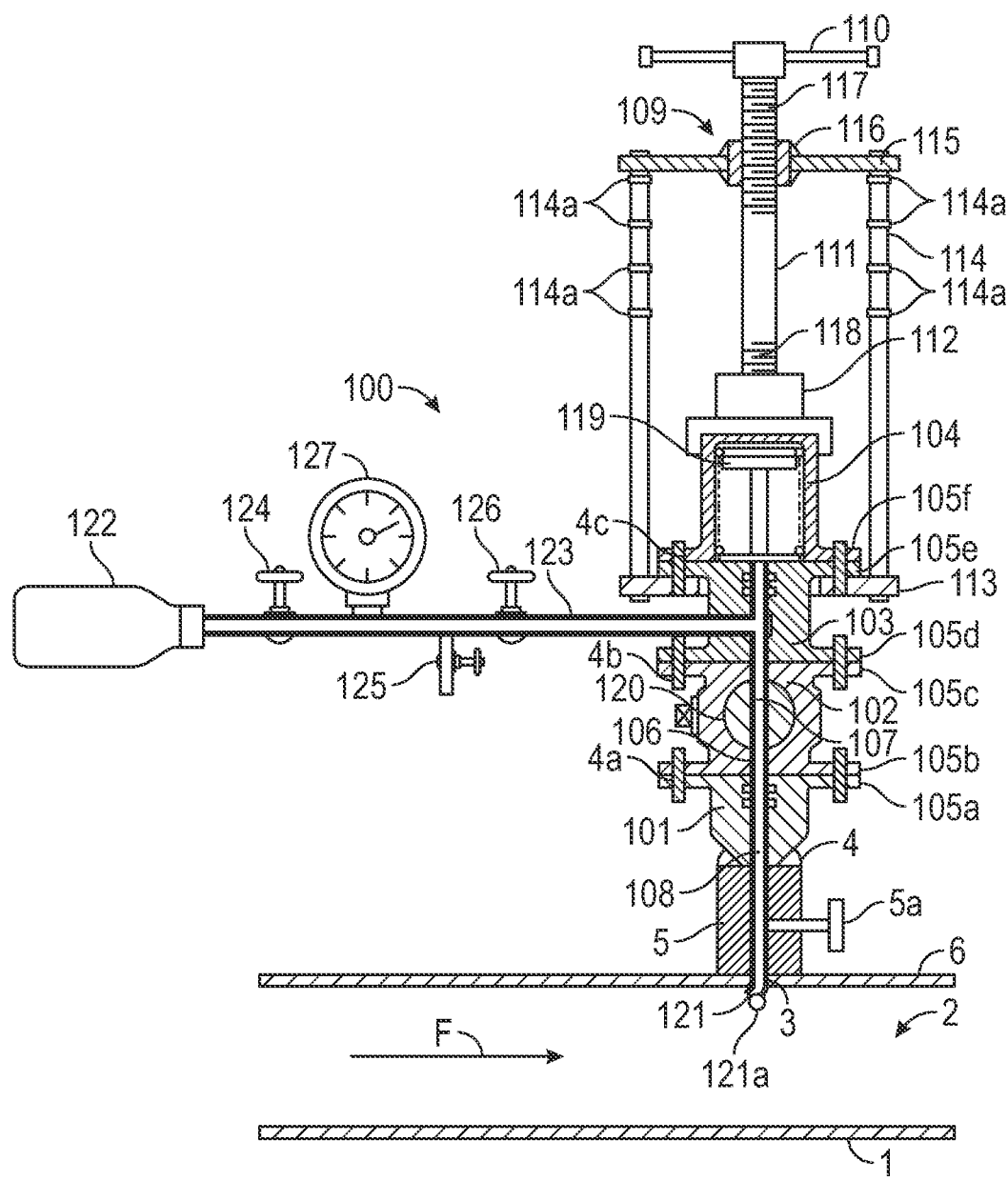

Now referring to FIG. 7, the valve 120 of the valve housing 102 is moved to the open position so that the continuous flow path 106 is open. The actuator housing 104 may be coupled on top of the cross-flow housing 103. For example, bottom flanges 105f of the actuator housing 104 mate on top of upper flanges 105e of the cross-flow housing 103. A mechanical fastener 4c, such as threaded connections, bolts, nuts, screws, studs, magnets, adhesives, and other type of non-permanent fasteners, may be used to couple the flanges 105e-f together. Additionally, the probe 107 is inserted into the continuous flow path 106 to extend downward from the actuator housing 104 and the inlet nozzle 121 enters the bore 2 of the pipeline 1. The probe 107 provides a fluid conduit from the bore of the pipeline to the sampling container In one or more embodiment, the actuator 109 may be coupled to the actuator housing 104. For example, the bottom plate 113 of the actuator 109 may be coupled to a surface of the upper flanges 105e of the cross-flow housing 104 opposite a surface of the upper flanges 105e mated with the bottom flanges 105f of the actuator housing 104. Additionally, the mechanical fastener 4c may also be used to couple the bottom plate 113 to the upper flanges 105e of the cross-flow housing 104. From the bottom plate 113, the guide rods 114 extend upward to the top plate 115. Additionally, the top plate 115 is positioned at a height on the guide rods 114. For example, the top plate 115 may be locked on various locking devices 114a of the guide rods 114 thereby limiting a distance the rod 111 may axially travel upward or downward. The height at which the top plate 115 is positioned may be based on a size (i.e., the inner diameter) of the pipeline 1. At the top plate, the torque connection (e.g., a hand wheel) 110 and the rod 111 are installed to be operationally coupled to the actuator housing 104 via the cap 112.

Figure 8:
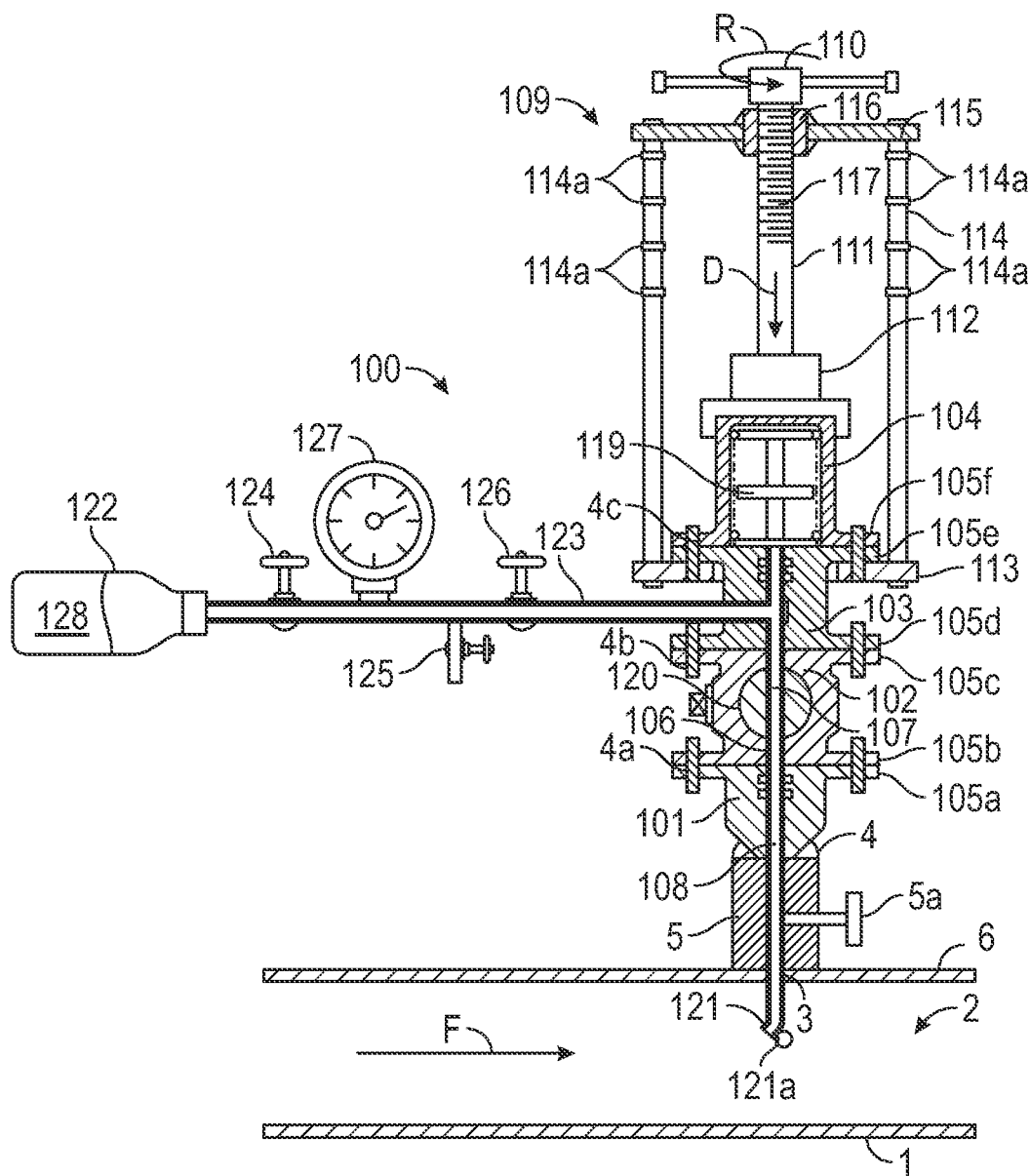
Figure 9:
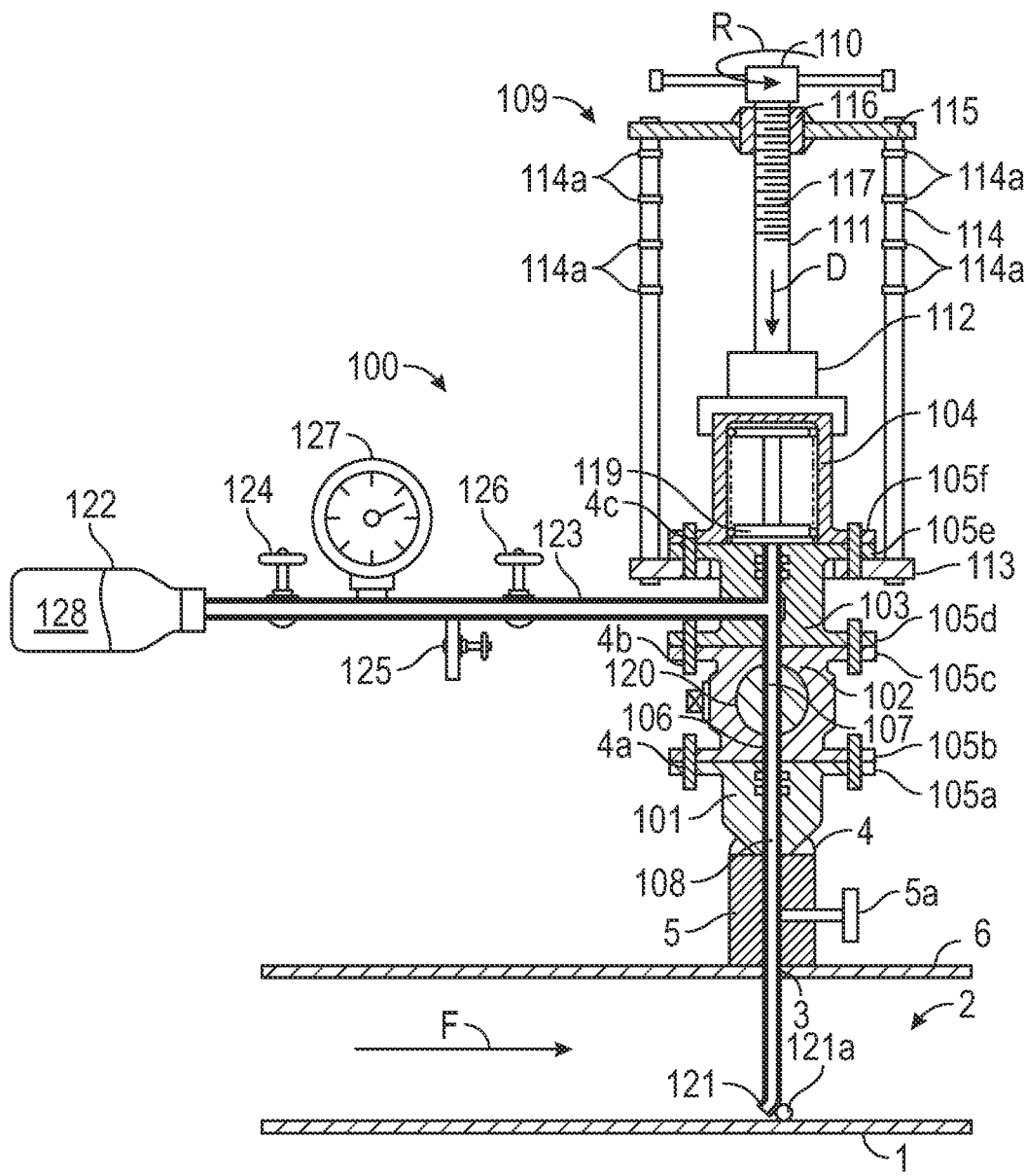

As shown in FIGS. 8 and 9, with the portable hydrocarbon sampling device 100 assembled and removably coupled to the pipeline 1, the actuator 109 is actuated to move the probe 107 and extend the inlet nozzle 121 into the bore 2 to reach the required depth. For example, the torque connection 110 is torqued in one direction (see Arrow R) to move the rod 111 axially downward (See arrow D) which is turn moves the actuation plate 119 downward thereby extending the inlet nozzle 121 into the bore. The inlet nozzle 121 may further include the position sensor 121a, such as a depth encoder, to determine when the inlet nozzle 121 reaches a required depth within the pipeline 1. The required depth may be based on a composition of the fluids within the pipeline 1 to avoid less water entering the fluid sample 128. FIG. 8 illustrates an example of where the inlet nozzle 121 is positioned along an axis of the bore 2. FIG. 9 illustrates an example of where the inlet nozzle 121 is positioned at a lowest point in the bore 2.

Figure 10:
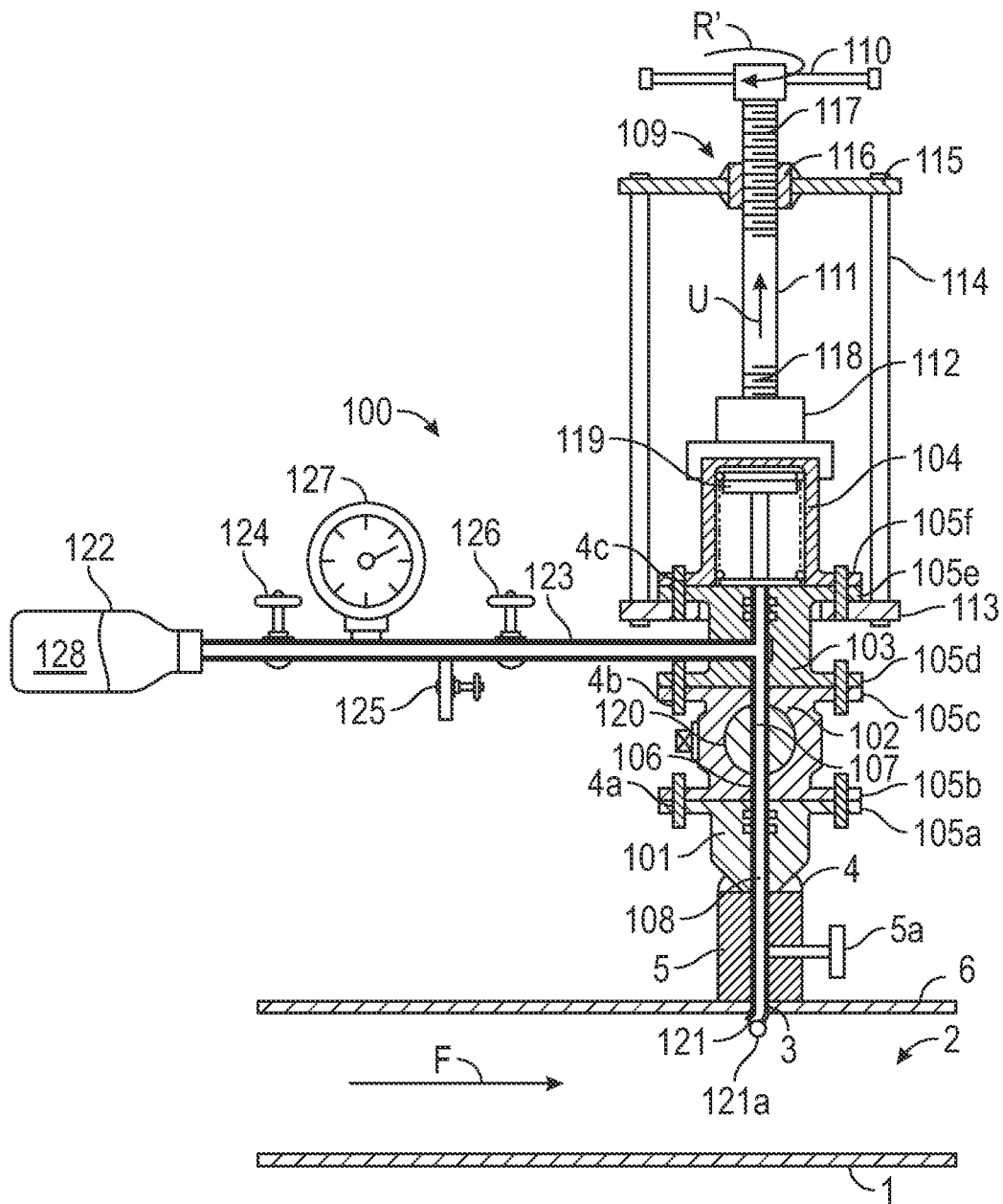

Now turning to FIG. 10, an example of actuating the actuator 109 in a reverse direction (Arrow R') is illustrated. For example, the torque connection is torqued in the reverse direction (Arrow R') to move the rod 111 axially upward (Arrow U) which is turn moves the actuation plate 118 axially upward thereby positioning the inlet nozzle 121 at a highest point in the bore 2.

As illustrated in FIGS. 8-10, with the inlet nozzle 121 in the bore 2, hydrocarbons from the pipeline 1 may flow up the probe 107 based a differential pressure between the bore 2 and the sampling container 122. With hydrocarbons being flowing into the probe via the inlet nozzle 121, the hydrocarbons travel up the probe 107 and into the cross bore 123 to be collected in the sampling container 122 as the hydrocarbon samples 128. In some embodiments, the pressure sensor 127 attached to the cross bore 123 measures the pressure within the cross bore 123 to monitor when the pressure matches the pressure in the bore 2 to determine that the sampling container 122 is filled.

One skilled in the art will appreciate how the double block (124, 126) and bleed (125) valve configuration on the cross bore 123 may be used to ensure the pressure is zero psi for the hydrocarbon samples 128 when it is time to remove the sampling container 122. With the hydrocarbon samples 128 collected in the sampling container 122, the sampling container 122 may be removed to be sent to a laboratory for analysis. In some embodiments, a second sampling container may be coupled to the distal end of the cross bore to replace the sampling container 122 if more hydrocarbon samples are required. However, if the hydrocarbon sampling operations are completed, the portable hydrocarbon sampling device 100 may be disassembled to be stored or sent to another location to take further hydrocarbon samples at different vent of the same or different pipeline.

In addition to the benefits described above, the portable hydrocarbon sampling device 100 may improve an overall efficiency and performance of hydrocarbon sampling operations while reducing cost and risk of non-productive time (NPT), and many other advantages. Further, the portable hydrocarbon sampling device 100 may provide further advantages such as being able to take hydrocarbon samples at any level inside a pipeline, using existing vents as access points to avoid needing fixed locations, easily transported to any site location, and many other advantages.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function(s) and equivalents of those structures. Similarly, any step-plus-function clauses in the claims are intended to cover the acts described here as performing the recited function(s) and equivalents of those acts. It is the express intention of the applicant not to invoke 35 U.S.C. § 112(f) for any limitations of any of the claims herein, except for those in which the claim expressly uses the words "means for" or "step for" together with an associated function.

What is claimed:

1. A method for conducting a hydrocarbon sampling operation on a pipeline, the method comprising:
   removably coupling a portable hydrocarbon sampling device to the pipeline to access a vent of the pipeline;
   actuating an actuator of the portable hydrocarbon sampling device in a first direction to extend a probe of the portable hydrocarbon sampling device into a bore of the pipeline through the vent;
   drawing hydrocarbons flowing in the bore into the probe and pushing the hydrocarbons up the probe and into a cross bore with a differential pressure between the bore and a sampling container fluidly coupled to the cross bore; and
   obtaining a hydrocarbon sample by collecting the hydrocarbons in the sampling container.

2. The method of claim 1, wherein removably coupling the portable hydrocarbon sampling device comprises removably coupling a first housing of the portable hydrocarbon on top of a vent valve.

3. The method of claim 1, wherein removably coupling the portable hydrocarbon sampling device comprises assembling the portable hydrocarbon sampling device on the pipeline.

4. The method of claim 3, assembling the portable hydrocarbon sampling device on the pipeline further comprising:
   coupling a first housing of the portable hydrocarbon sampling device on top of a vent valve on an outer surface of the pipeline, wherein a first bore of the first housing is coaxial with the vent;
   coupling a valve housing of the portable hydrocarbon sampling device on top of the first housing, wherein a second bore of the valve housing is coaxial with the first bore of the first housing;
   coupling a cross-flow housing of the portable hydrocarbon sampling device on top of the valve housing, wherein a third bore of the cross-flow housing is coaxial with the second bore of the valve housing;
   forming a continuous flow path with the first bore, the second bore, and the third bore;
   coupling a cross bore to the cross-flow housing, wherein the cross bore is perpendicular to and in fluid communication with the continuous flow path;
   inserting the probe into the continuous flow path and extending an inlet nozzle of the probe into the bore; and
   coupling an actuator housing of the portable hydrocarbon sampling device on top of the cross-flow housing.

5. The method of claim 4, further comprising actuating a valve of the valve housing to an open position.

6. The method of claim 1, wherein actuating the actuator further comprises torquing a torque connection of the actuator.

7. The method of claim 1, further comprising:
   closing a vent valve on the pipeline;
   closing two block valves on the cross bore;
   opening a bleed valve between the two block valves; and
   bleeding air through the bleed valve to reduce a pressure in the cross bore to zero psi.

8. The method of claim 7, further comprising monitoring a pressure within the cross bore with a pressure sensor.

9. The method of claim 8, further comprising removing the sampling container and transporting the sampling container to a laboratory.

10. A portable hydrocarbon sampling device, comprising:
    a first housing with a first bore;
    a valve housing with a second bore coupled to the first housing, wherein the valve housing comprises a valve to open and close the second bore;
    a cross-flow housing with a third bore coupled to the valve housing, wherein the first bore, the second bore, and the third bore form a continuous flow path;
    a cross bore coupled to the cross-flow housing, wherein the cross bore is perpendicular to the third bore;
    a probe disposed within the continuous flow path and in fluid communication with the cross bore;

an actuator housing coupled to the cross-flow housing, wherein the actuator housing comprises an actuator to extend into the probe; and a sampling container fluidly coupled to the cross bore at end distal to the cross-flow housing, wherein the sampling container is configured to collect the fluids from the probe.

11. The portable hydrocarbon sampling device of claim 10, further comprising two block valves provided on the cross bore, and a bleed valve provided on the cross bore between the two block valves.

12. The portable hydrocarbon sampling device of claim 11, further comprising a pressure sensor provided on the cross bore between the two block valves.

13. The portable hydrocarbon sampling device of claim 10, wherein the probe comprises an inlet nozzle extending out of an opening of the first housing.

14. The portable hydrocarbon sampling device of claim 10, wherein the actuator comprises a torque connection and a rod configured to axially move an actuator plate.

15. A system comprising:

a pipeline defining a bore with hydrocarbons flowing therein, wherein the pipeline includes a plurality of vents; and a portable hydrocarbon sampling device removably coupled to the pipeline at a location of a vent of the plurality of vents, wherein the portable hydrocarbon sampling device comprises:

a first housing with a first bore and an opening coaxial with the vent;

a valve housing with a second bore coupled on top of the first housing, wherein the valve housing comprises a valve to open and close the second bore;

a cross-flow housing with a third bore coupled on top of the valve housing, wherein the first bore, the second bore, and the third bore form a continuous flow path in fluid communication with the bore;

a cross bore coupled to the cross-flow housing, wherein the cross bore is perpendicular to the third bore;

a probe disposed within the continuous flow path and in fluid communication with the cross bore and bore;

an actuator housing coupled on top of the cross-flow housing, wherein the actuator housing includes an actuator configured to extend the probe into the bore; and a sampling container fluidly coupled to the cross bore at end distal to the cross-flow housing, wherein the sampling container is configured to collect the hydrocarbons from the probe.

16. The system of claim 15, wherein the location of the vent is approximate to a transfer point where the hydrocarbons exit the pipeline.

17. The system of claim 15, further comprising mechanical fasteners configured to couple the first housing to a vent valve on an outer surface of the pipeline, wherein the vent valve covers the vent of the plurality of vents.

18. The system of claim 15, wherein the cross bore comprises two block valves and a bleed valve between the two block valves.

19. The system of claim 18, further comprising a pressure sensor provided on the cross bore between the two block valves.

20. The system of claim 15, wherein an inlet nozzle of the probe is positioned within a bore at a depth based on a level at which the hydrocarbons flow within the bore.

* * * * *